(12) United States Patent
Goff et al.

(10) Patent No.: US 8,700,131 B2
(45) Date of Patent: Apr. 15, 2014

(54) RADIAL CARDIAC CATHETERIZATION BOARD

(75) Inventors: Gary Goff, Canton, GA (US); L. Van Thomas Crisco, Atlanta, GA (US)

(73) Assignee: Merit Medical Systems, Inc., South Jordan, UT (US)

( * ) Notice: Subject to any disclaimer, the term of this patent is extended or adjusted under 35 U.S.C. 154(b) by 322 days.

(21) Appl. No.: 13/030,858

(22) Filed: Feb. 18, 2011

(65) Prior Publication Data

US 2011/0184278 A1    Jul. 28, 2011

Related U.S. Application Data

(63) Continuation-in-part of application No. 12/777,871, filed on May 11, 2010, now Pat. No. 8,369,933.

(60) Provisional application No. 61/216,075, filed on May 13, 2009.

(51) Int. Cl.
   *A61B 6/00*    (2006.01)

(52) U.S. Cl.
   USPC ............... 600/424; 600/427; 5/601; 5/623; 5/694

(58) Field of Classification Search
   USPC ............ 5/601, 623, 694; 600/424, 427, 407; 378/165
   See application file for complete search history.

(56) References Cited

U.S. PATENT DOCUMENTS

| | | | |
|---|---|---|---|
| 4,369,774 A | 1/1983 | Robbins | |
| 4,662,366 A | 5/1987 | Tari | |
| 4,665,574 A * | 5/1987 | Filips et al. | 5/694 |
| 4,674,110 A | 6/1987 | Eaton et al. | |
| 5,263,497 A | 11/1993 | Grabenkort et al. | |
| 5,291,903 A | 3/1994 | Reeves | |
| 5,339,834 A | 8/1994 | Marcelli | |
| 5,342,290 A | 8/1994 | Schuellein | |
| 5,372,145 A | 12/1994 | Berger | |
| 5,549,121 A * | 8/1996 | Vinci | 128/878 |

(Continued)

FOREIGN PATENT DOCUMENTS

| GB | 2472246 A | 2/2011 |
|---|---|---|
| WO | 2005090072A1 A1 | 9/2005 |

OTHER PUBLICATIONS

International Searching Authority, International Search Report and Written Opinion for PCT/US2010/034452 mailed May 11, 2010.

(Continued)

*Primary Examiner* — Baisakhi Roy
(74) *Attorney, Agent, or Firm* — Stoel Rives LLP

(57) ABSTRACT

Embodiments of the present description provide a medical apparatus for use in supporting a patient lying in a supine position during a radial cardiac catheterization procedure. More particularly, embodiments of the present description provide an arm board a patient's arm during a radial cardiac catheterization procedure. The arm board has a base member having a substantially planar support surface on which the patient's arm can be stabilized during a catheterization procedure and at least one shield member affixed to the base member and extending away from the support surface. Desirably, the base member has both a radiolucent portion and a radiopaque portion and the shield member is a radiopaque material, thereby reducing and/or eliminating a doctor's exposure to radiation during radial cardiac catheterization procedures without impairing the ability to obtain the necessary medical images. Also provided is a medical apparatus and a method for its use.

17 Claims, 17 Drawing Sheets

(56) References Cited

U.S. PATENT DOCUMENTS

| | | | |
|---|---|---|---|
| 5,601,597 | A | 2/1997 | Arrowood et al. |
| 5,623,951 | A | 4/1997 | Kamaya |
| 5,785,057 | A | 7/1998 | Fischer |
| 5,845,643 | A | 12/1998 | Vergano et al. |
| 5,940,912 | A | 8/1999 | Keselman et al. |
| 5,981,964 | A | 11/1999 | McAuley et al. |
| 6,101,650 | A * | 8/2000 | Omdal et al. .................. 5/623 |
| 6,153,666 | A | 11/2000 | Lagace |
| 6,267,115 | B1 | 7/2001 | Marshel |
| 6,357,066 | B1 * | 3/2002 | Pierce ............................. 5/710 |
| 6,378,149 | B1 | 4/2002 | Sanders et al. |
| 6,467,487 | B1 | 10/2002 | Rios |
| 6,568,010 | B1 | 5/2003 | Ames |
| 6,647,986 | B1 | 11/2003 | Korotko et al. |
| 6,663,055 | B2 | 12/2003 | Boucher et al. |
| 6,725,481 | B1 | 4/2004 | Marshall |
| 6,898,810 | B2 | 5/2005 | Steven |
| 7,020,917 | B1 | 4/2006 | Kolody et al. |
| 7,057,194 | B2 * | 6/2006 | Goldstein ................. 250/515.1 |
| 7,274,031 | B2 | 9/2007 | Smith |
| 7,406,967 | B2 | 8/2008 | Callaway |
| 7,520,007 | B2 | 4/2009 | Skripps |
| 7,978,825 | B2 * | 7/2011 | Ngo ............................. 378/165 |
| 8,369,933 | B2 * | 2/2013 | Crisco et al. ................. 600/424 |
| 2002/0080921 | A1 * | 6/2002 | Smith et al. .................. 378/189 |
| 2004/0143177 | A1 | 7/2004 | Falbo, Sr. et al. |
| 2004/0216233 | A1 | 11/2004 | Ludwig et al. |
| 2005/0043805 | A1 * | 2/2005 | Chudik ....................... 623/19.14 |
| 2005/0091749 | A1 | 5/2005 | Humbles |
| 2006/0016006 | A1 * | 1/2006 | Whitmore et al. .................. 5/601 |
| 2006/0200061 | A1 | 9/2006 | Warkentine |
| 2007/0011814 | A1 | 1/2007 | Rotert |
| 2007/0152197 | A1 | 7/2007 | Lagrace et al. |
| 2007/0286340 | A1 | 12/2007 | Cadwalader et al. |
| 2008/0245373 | A1 | 10/2008 | Kounkel |
| 2009/0172884 | A1 | 7/2009 | Semlitsch |
| 2010/0305431 | A1 * | 12/2010 | Crisco et al. .................. 600/424 |
| 2011/0184278 | A1 * | 7/2011 | Goff et al. ..................... 600/427 |
| 2012/0170710 | A1 * | 7/2012 | Niedzielski et al. ............ 378/20 |
| 2012/0241652 | A1 * | 9/2012 | Jeschke ....................... 250/519.1 |

OTHER PUBLICATIONS

Brasselet, et al., "Comparison of Operator Radiation Exposure with Optimized Radiation Protection Devices During Coronary Angiograms and Ad Hoc Percutaneous Coronary Interventions by Radial and Femoral Routes," European Heart Journal (2008) 29:63-70.

Pristipino, et al., "Major Improvement of Percutaneous Cardiovascular Procedure Outcomes with Radial Artery Catherterisation: Results from the Prevail Study," Heart (British Cardiac Society) (2009) 95:476-82.

* cited by examiner

RADIAL CARDIAC CATHETERIZATION BOARD

CROSS-REFERENCE TO RELATED APPLICATIONS

The present application is a continuation-in-part of U.S. patent application Ser. No. 12/777,871, filed May 11, 2010, which claims benefit of U.S. Provisional Application No. 61/216,075, filed May 13, 2009. These applications are incorporated herein by reference.

BACKGROUND

The present description relates generally to an operating table extension useful for radial cardiac catheterization procedures. In particular, the present description relates to an arm board for use in radial cardiac catheterization procedures having both a radiolucent portion and a radiopaque portion.

Coronary diseases remain a leading cause of morbidity and mortality in Western societies and are treated using a number of approaches. It is often sufficient to treat the symptoms with pharmaceuticals and lifestyle modification to lessen the underlying causes of the disease. In more severe cases, however, it may be necessary to treat the coronary disease using interventional medical procedures such as cardiac catheterization. Cardiac catheterization procedures generally utilize a thin catheter passed through a major artery to access a patient's heart. In the United States, the femoral artery is most frequently used during cardiac catheterization procedures. Recent medical advancements, however, suggest that use of the radial artery is more convenient and may reduce both the length of the procedure and the risk of complications during the procedure. Despite these benefits, many doctors still remain reluctant to perform cardiac catheterization via the radial artery because the procedure requires the doctor to stand closer to the source of radiation for the medical imaging (e.g., x-ray photography), exposing the doctor to significantly more radiation during the procedure than the doctor typically is exposed to during femoral catheterization procedures.

Existing equipment used for positioning the patient's arm during radial cardiac catheterization procedures have numerous drawbacks that make it difficult for doctors to perform cardiac catheterization via the radial artery. For example, existing arm boards are made entirely of radiolucent materials that do not interfere with the medical imaging necessary during the procedure. The radiolucent materials, however, do not provide any protection from the radiation to the doctor performing the procedure. In addition, existing arm boards generally are of both an insufficient size and shape for performing cardiac catheterization and coronary intervention as they are not sufficiently supportive for the technical aspects of intervention. Cardiac catheterization procedures often require use of numerous surgical instruments including wires, guides, balloons, and stents, and many doctors prefer having a larger more supportive space upon which to manipulate these instruments. Cardiac catheterization procedures also can be very time consuming and result in loss of a large amount of blood from the patient. Existing arm boards used for positioning the patient's arm during cardiac catheterization procedures, however, have no means for containing the blood which ultimately flows off of the operating table and onto the surgeon or floor, and are not readily supportive for interventional instruments.

Accordingly, there exists a need for an arm board suitable for use during radial cardiac catheterization procedures. Desirably, the arm board should be designed using materials that can reduce and/or eliminate a doctor's exposure to radiation during the procedure without impairing the ability to obtain the necessary medical images during the procedure. Moreover, the arm board desirably also should be of a size and shape suitable for addressing other drawbacks of existing arm boards.

BRIEF SUMMARY OF THE DESCRIPTION

Briefly described, embodiments of the present description address the above-described needs by providing an arm board for use in a radial cardiac catheterization procedure. The arm board comprises a base member having a substantially planar support surface on which a patient's arm can be stabilized during a catheterization procedure, the base member comprising at least one radiolucent portion and at least one radiopaque portion. The arm board further comprises at least one shield member affixed to the base member and extending away from the support surface at an angle from about 30 and about 90 degrees, the shield member comprising a radiopaque material.

Embodiments of the present description further provide a medical apparatus for use in supporting a patient lying in a supine position during a radial cardiac catheterization procedure. The medical apparatus comprises an operating table suitable for supporting a patient lying in the supine position and an arm board secured to the operating table. The arm board comprises a base member having a substantially planar support surface on which a patient's arm can be suitably stabilized during a catheterization procedure, the base member comprising at least one radiolucent portion and at least one radiopaque portion. The arm board further comprises at least one shield member affixed to the base member and extending away from the support surface at an angle from about 30 and about 90 degrees, the shield member comprising a radiopaque material.

Embodiments of the present description still further provide a method for radial cardiac catheterization of a patient, the method comprising supporting the arm of a patient lying in a supine position on an operating table, introducing one or more medical instruments through a catheter in the stabilized arm of the patient, and using x-ray imaging to visualize the position of the one or more medical instruments introduced into the patient through the catheter. The arm is supported by an arm board which extends from the operating table and comprises a base member having a substantially horizontal and planar support surface on which the arm is stabilized and at least one shield member affixed to the base member and extending away from the support surface at an angle from about 30 and about 90 degrees. The base member of the arm board comprises a radiolucent portion positioned in the arm board to permit said x-ray imaging and a radiopaque portion surrounding at least part of the radiolucent portion while the shield member of the arm board comprises a radiopaque material.

Additional aspects will be set forth in part in the description and drawings which follow, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Embodiments of the present description provide an arm board for use in a radial cardiac catheterization procedure. The arm board comprises a substantially planar member having a support surface on which a patient's arm can be stabilized during a catheterization procedure. Desirably, the member comprises at least one radiolucent portion and at least one radiopaque portion. The term "radiolucent," as used herein, means a material that substantially permits the penetration and passage of x-rays or other forms of radiation through the material. The term "radiopaque," as used herein, means a material that substantially prevents the penetration and passage of x-rays or other forms of radiation through the material.

Figure 1:
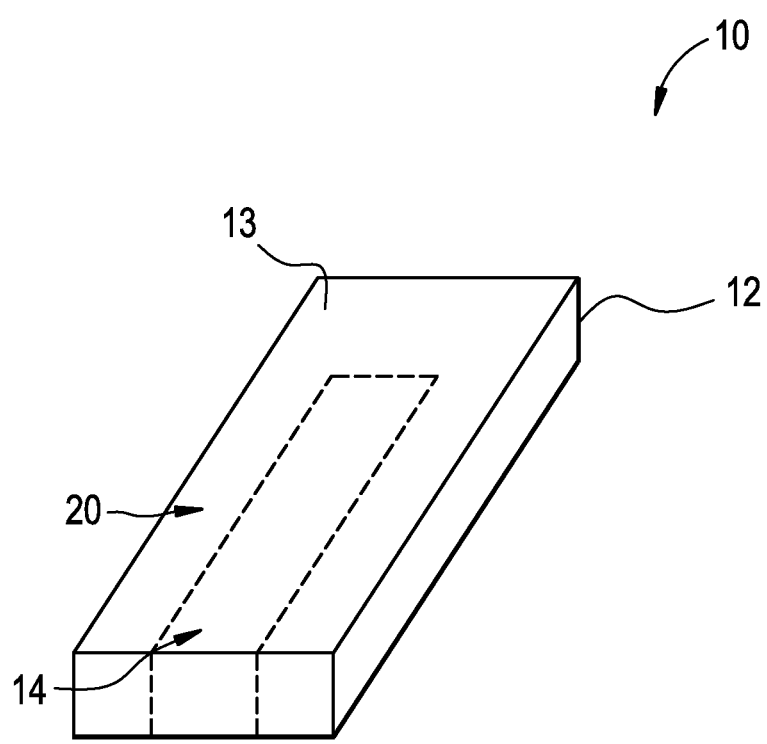
FIG. 1 is a perspective view of an arm board according to a particular embodiment.

In one aspect, illustrated in FIG. 1, an arm board 10 is provided for use in a radial cardiac catheterization procedure. The arm board 10 comprises a base member 12 that is substantially planar and having a support surface 13 on which a patient's arm can be stabilized during a catheterization procedure. The substantially planar member 12 of the arm board can be any shape that is suitable for providing a support surface on which a patient's arm can be stabilized during a catheterization procedure. For example, the substantially planar member 12 can be elliptical, rectangular, oblong (FIG. 2), oval, square, L-shaped (FIG. 10), or U-shaped (FIG. 3).

Figure 2:
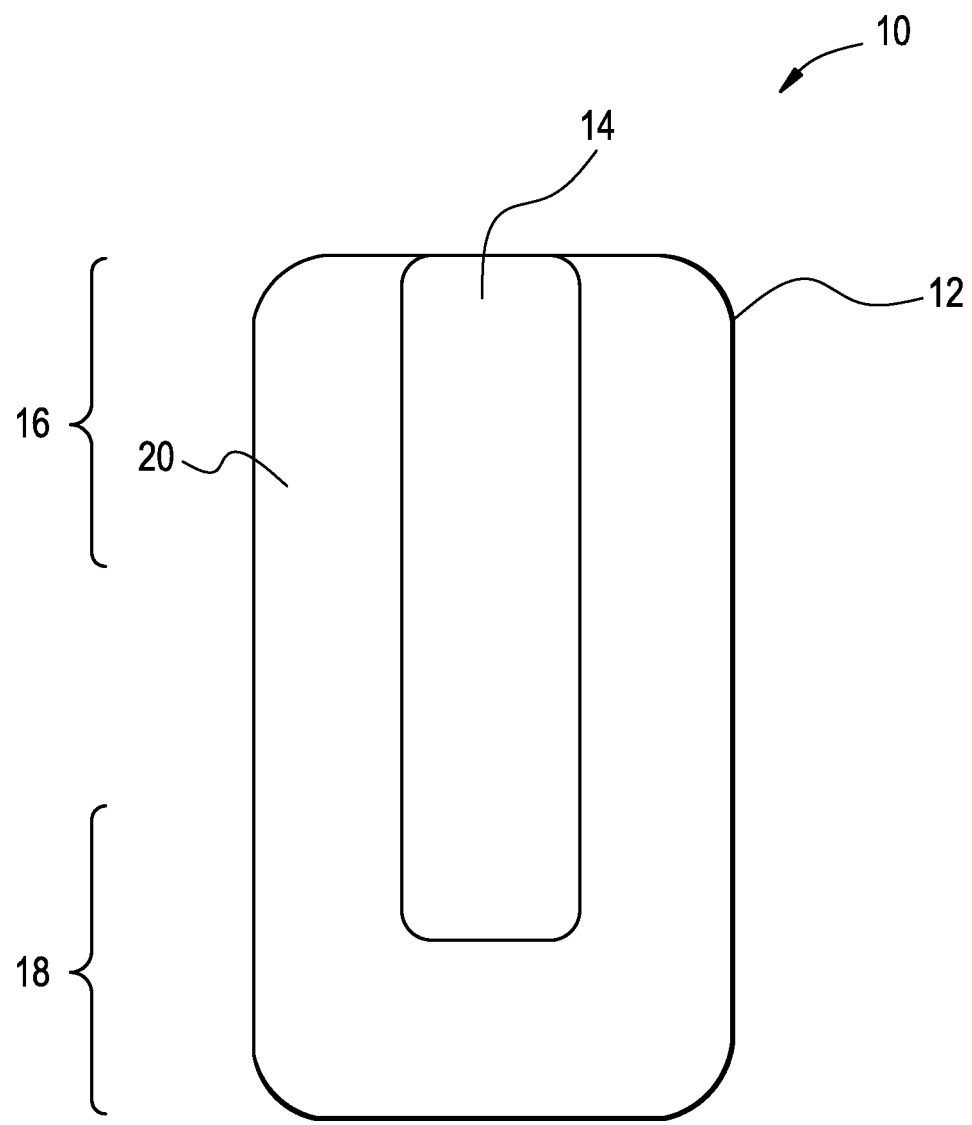
FIG. 2 is an illustration of an arm board according to a particular embodiment.
Figure 3A:
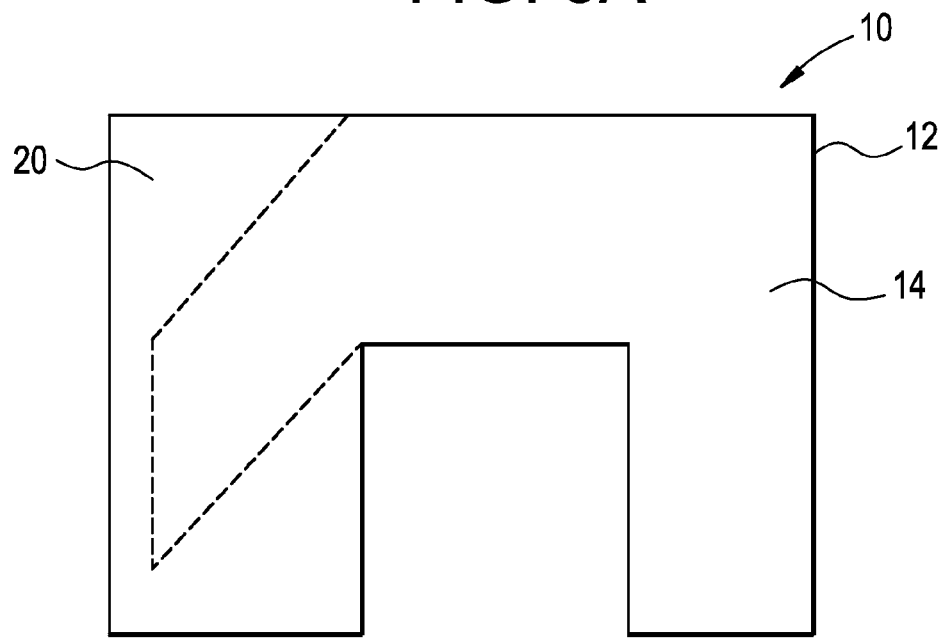
FIGS. 3A and 3B are illustrations of an arm board according to particular embodiments.
Figure 3B:
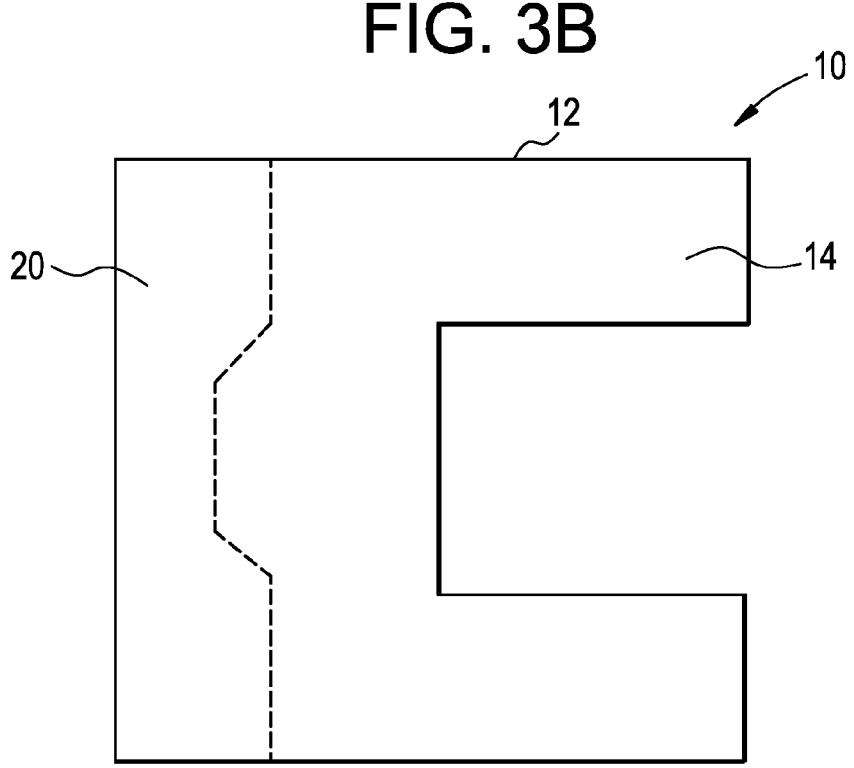
Figure 4A:
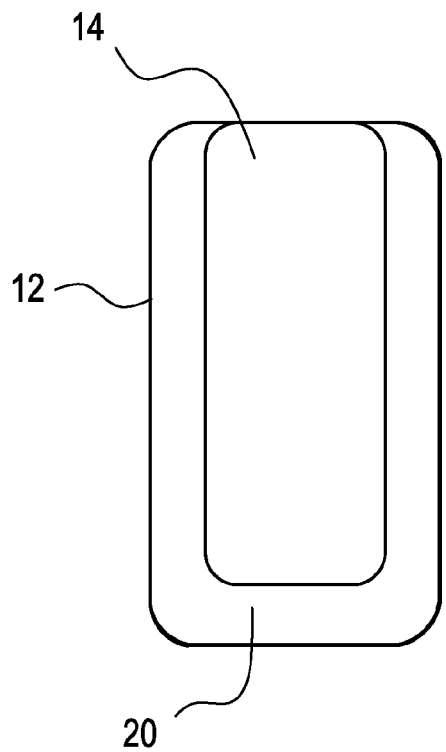
FIGS. 4A, 4B, and 4C are illustrations of an arm board having an adjustable radiopaque portion according to particular embodiments.
Figure 4B:
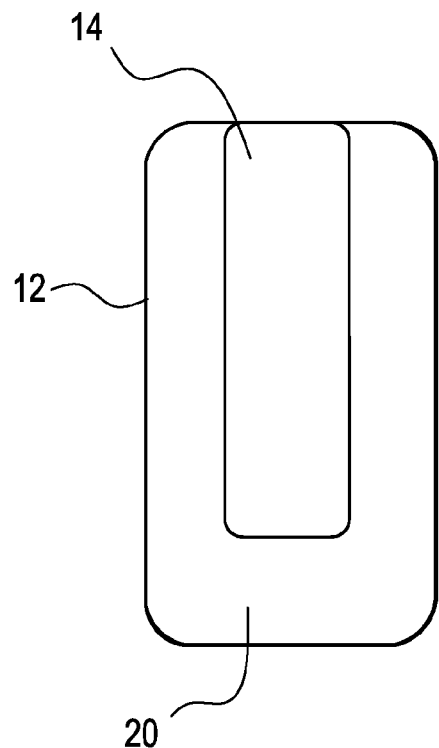
Figure 4C:
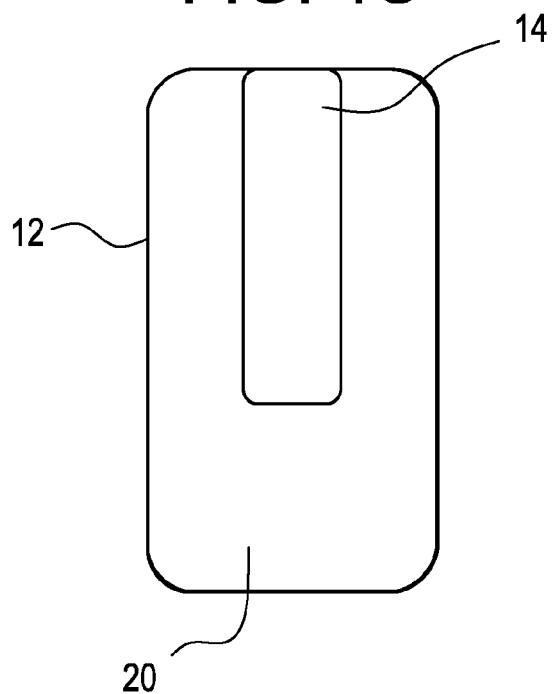

In one aspect, illustrated in FIG. 2, the at least one radiolucent portion 14 of the member 12 has an area corresponding at least substantially to an area on the support surface 13 on which the patient's arm would be stabilized during a catheterization procedure. The member 12 is elongated in at least one direction and comprises a radiolucent portion 14 extending from a first end 16 of the member 12 along a medial section of the member toward an opposed second end 18. The at least one radiopaque portion 20 of the member 12 may have an area lateral to at least a portion of the area of the radiolucent portion 14. In one aspect, the at least one radiopaque portion 20 of the member 12 surrounds at least part of the radiolucent portion 14 at the second end of the member 18. In another aspect, the position of at least part of the radiopaque portion 20 is adjustable within the member 12 (FIG. 4), such that the area of the member 12 comprising the radiopaque portion 20 can be increased or decreased depending on the need for medical imaging.

In one aspect, the radiolucent portion 14 comprises between about 5% and about 50% of the area of the support surface of the member 12. In still other aspects, the radiolucent portion 14 comprises between about 5% and about 40%, about 5% and about 30%, or about 5% and about 25% of the area of the support surface of the member 12. In one aspect, the radiopaque portion 20 comprises between about 20% and about 80% of the area of the support surface of the member 12. In still other aspects, the radiopaque portion 16 comprises between about 40% and about 80%, about 60% and about 80%, or about 75% and about 80% of the area of the support surface member 12.

Figure 5A:
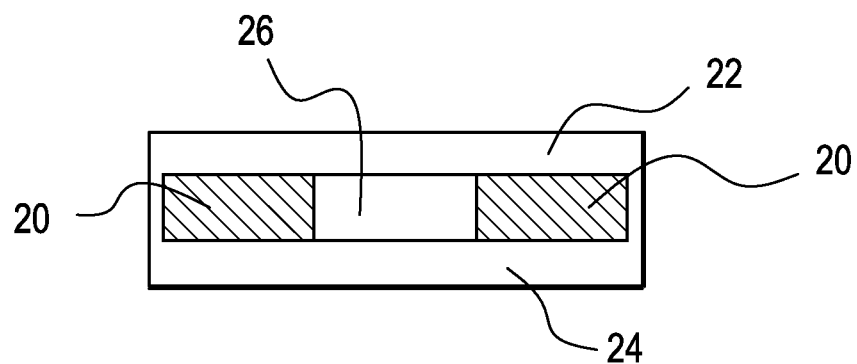
FIGS. 5A and 5B are side cross-sectional views of an arm board according to a particular embodiment.
Figure 5B:
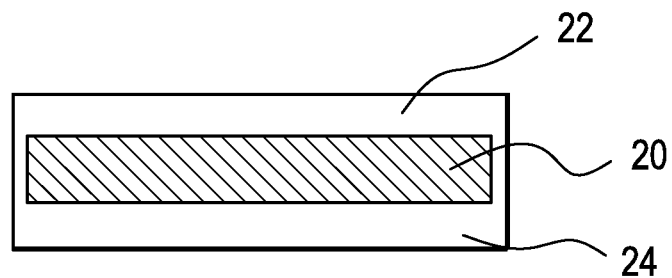
Figure 6A:
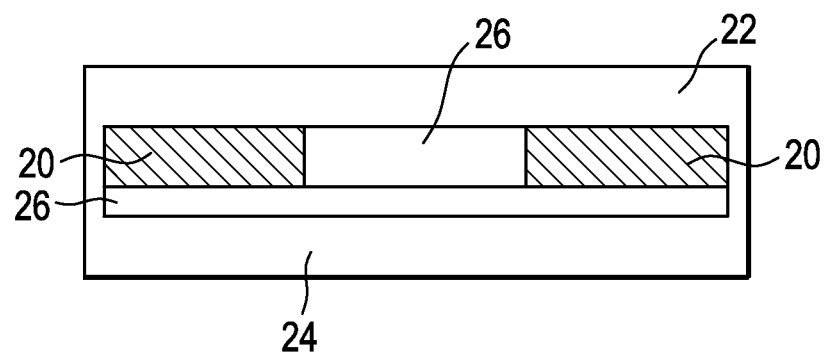
FIGS. 6A and 6B are side cross-sectional view of an arm board according to a particular embodiment.
Figure 6B:
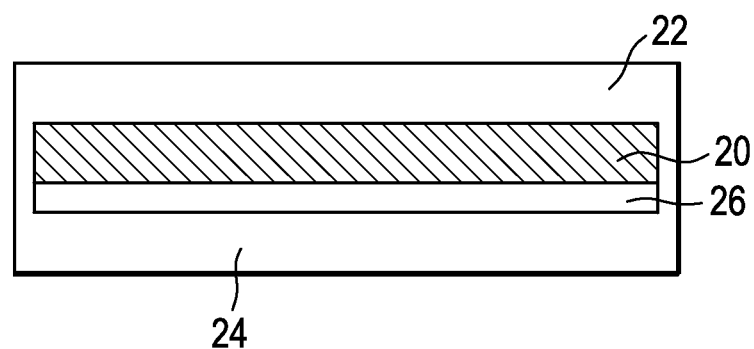
Figure 7A:
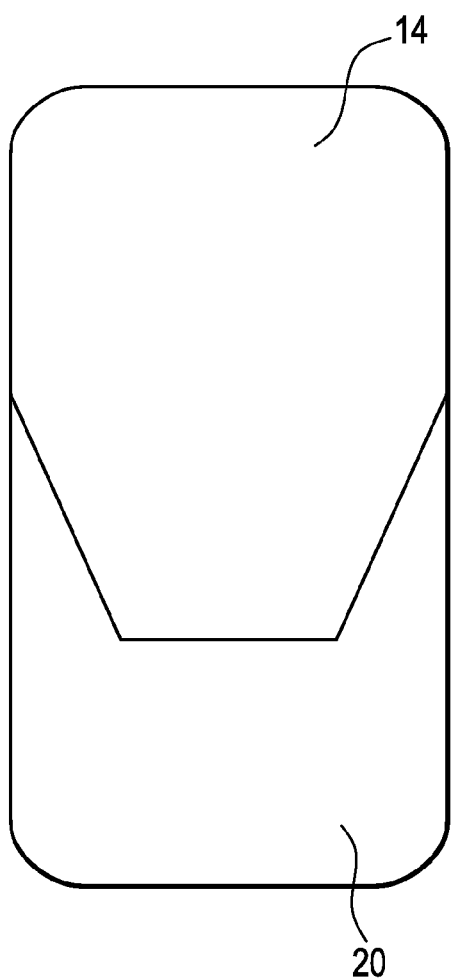
FIGS. 7A and 7B are illustrations of arm boards according to particular embodiments.
Figure 7B:
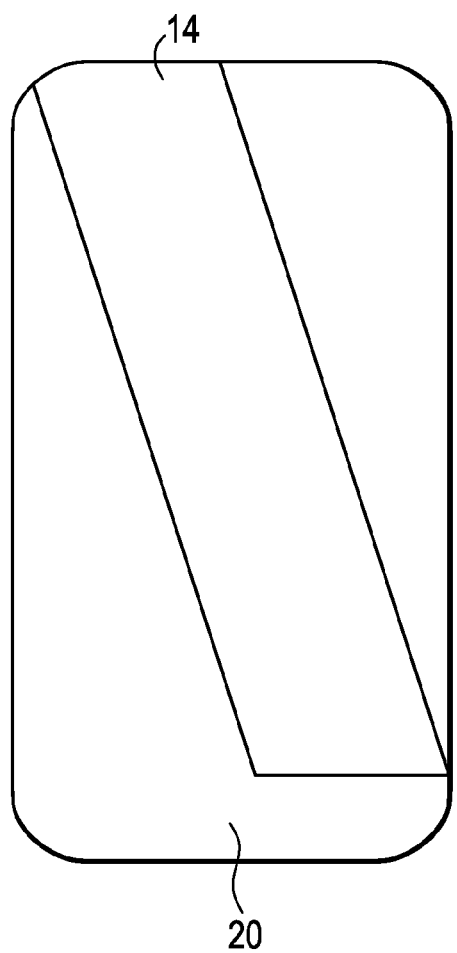

In particular embodiments, the substantially planar member 12 is a multilayer composite structure comprising one or more layers. The one or more layers can comprise any suitable combination of materials, non-limiting examples of which include a radiolucent structural material, a substantially waterproof radiolucent material, a radiation-absorbing material, an adhesive, or combinations thereof. In one embodiment illustrated in FIG. 5, the substantially planar member 12 comprises in a traverse cross-section an upper outer layer 22, an opposed lower outer layer 24, and, at least in the radiopaque portion 20, one or more inner layers 26 disposed between the upper outer layer 22 and the lower outer layer 24. In one aspect, the upper and lower outer layers 22, 24 comprise a substantially waterproof radiolucent material. In another aspect, the one or more inner layers 26 comprise a radiolucent structural material. In still another aspect illustrated in FIG. 6, the one or more inner layers 26 comprise a radiation-absorbing material positioned in the radiopaque portion 20 of the member 12. In still another aspect, the one or more of the inner layers 26 comprise an adhesive for bonding together the one or more inner layers 26 and the upper and lower outer layers 22, 24. Those skilled in the art will appreciate that the one or more layers of such multilayer composite structures may be disposed in any orientation suitable for providing a substantially planar member 12 having at least one radiolucent portion 14 and at least one radiopaque portion 20. Those skilled in the art also will appreciate that the radiolucent portion 12 and radiopaque portion 20 may be disposed in any orientation suitable for positioning the radiolucent portion of the board substantially beneath the patient's arm so that the desired medical images can be obtained (FIG. 7).

The arm board provided herein may be prepared using any materials suitable for providing a substantially planar member having both at least one radiolucent portion and at least one radiopaque portion.

In one aspect, the radiopaque portion 20 of the member 12 desirably comprises a radiation-absorbing material capable of providing a radiation attenuation equivalence of at least that of a 0.25 mm lead sheet. Materials suitable for absorbing radiation are well known to those skilled in the art, and include metals, metal oxides, metal salts, or alloys comprising a metallic component with an atomic number greater than 45. Non-limiting examples of metallic components include antimony, tin, barium, bismuth, cesium, cadmium, indium, rhodium, tungsten, uranium, lead, and combinations thereof.

Radiation-absorbing materials and methods for preparing radiation-absorbing materials suitable for use in the radiopaque portion 20 of the member 12 of the arm board 10 provided in embodiments herein are further described in detail in U.S. Pat. Nos. 6,153,666 and 7,274,031 and in U.S. Patent Publication No. 2007/0152197, the relevant disclosures of which are incorporated herein by reference.

In one aspect, the radiolucent portion 14 of the member 12 comprises a radiolucent material. Those skilled in the art will appreciate that any material that is substantially radiolucent can be used in the radiolucent portion of the arm board. For example in a particular embodiment the composite material comprises a fiber-reinforced polymer, an aramid (e.g., a para-aramid synthetic fiber or other aromatic polyamide), a polyethylene (e.g., a high molecular weight polyethylene, ultra high molecular weight polyethylene, etc.), a wood or wood composite (e.g., plywood), or any other polymer or composite material that is substantially radiolucent.

Figure 8:
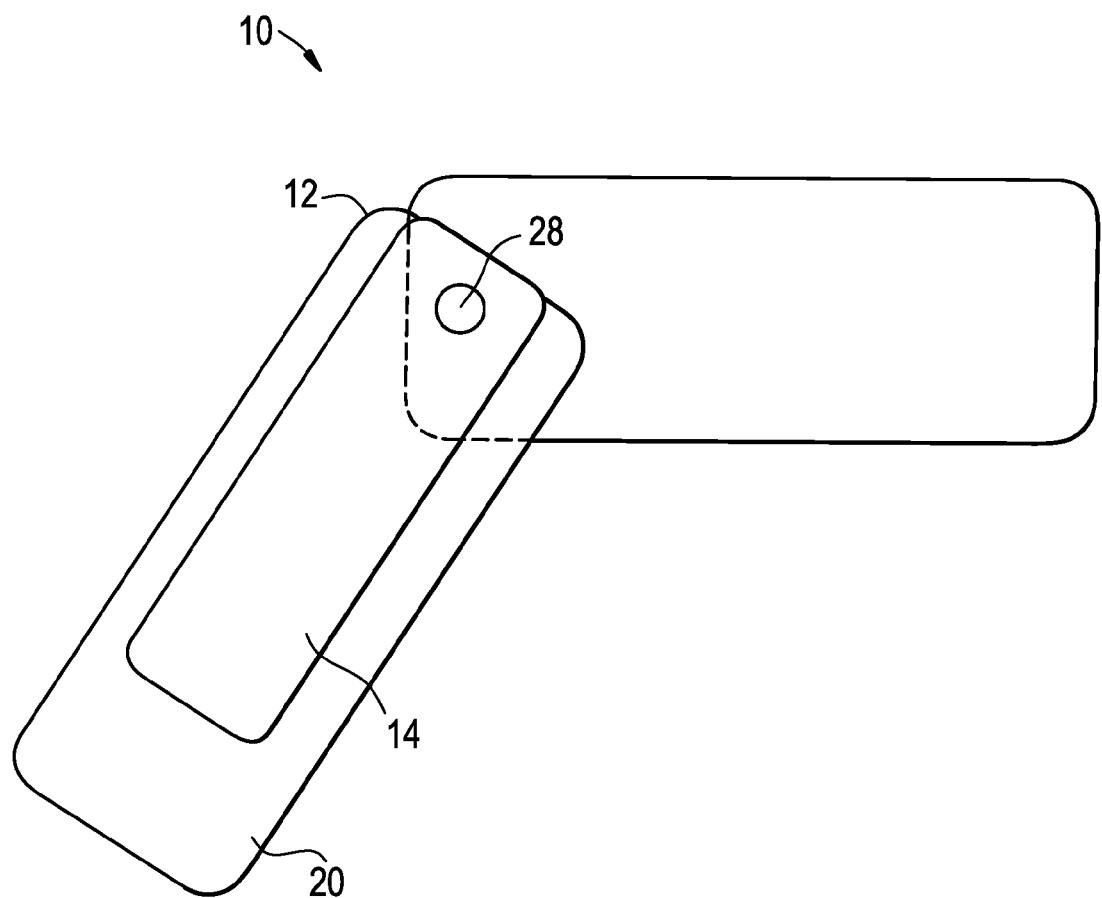
FIG. 8 is an illustration of an arm board comprising a hinge according to a particular embodiment.
Figure 9:
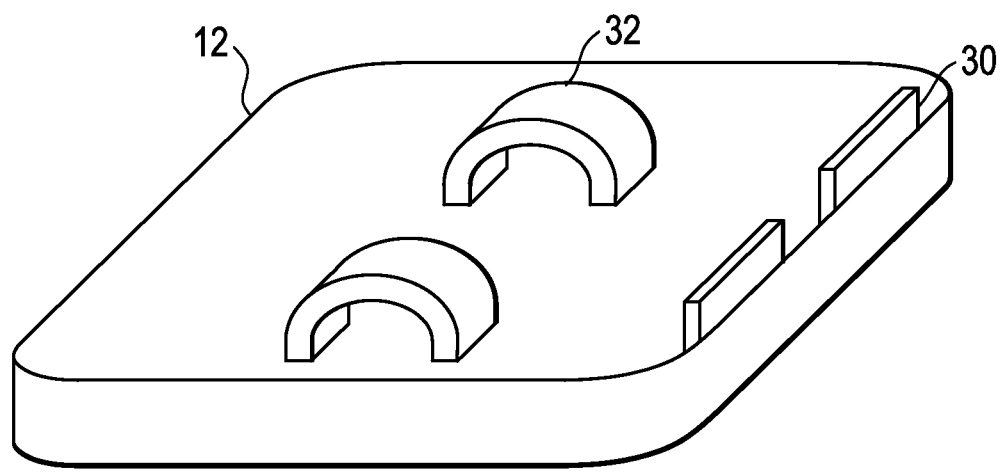
FIG. 9 is a perspective view of an arm board according to a particular embodiment.
Figure 10A:
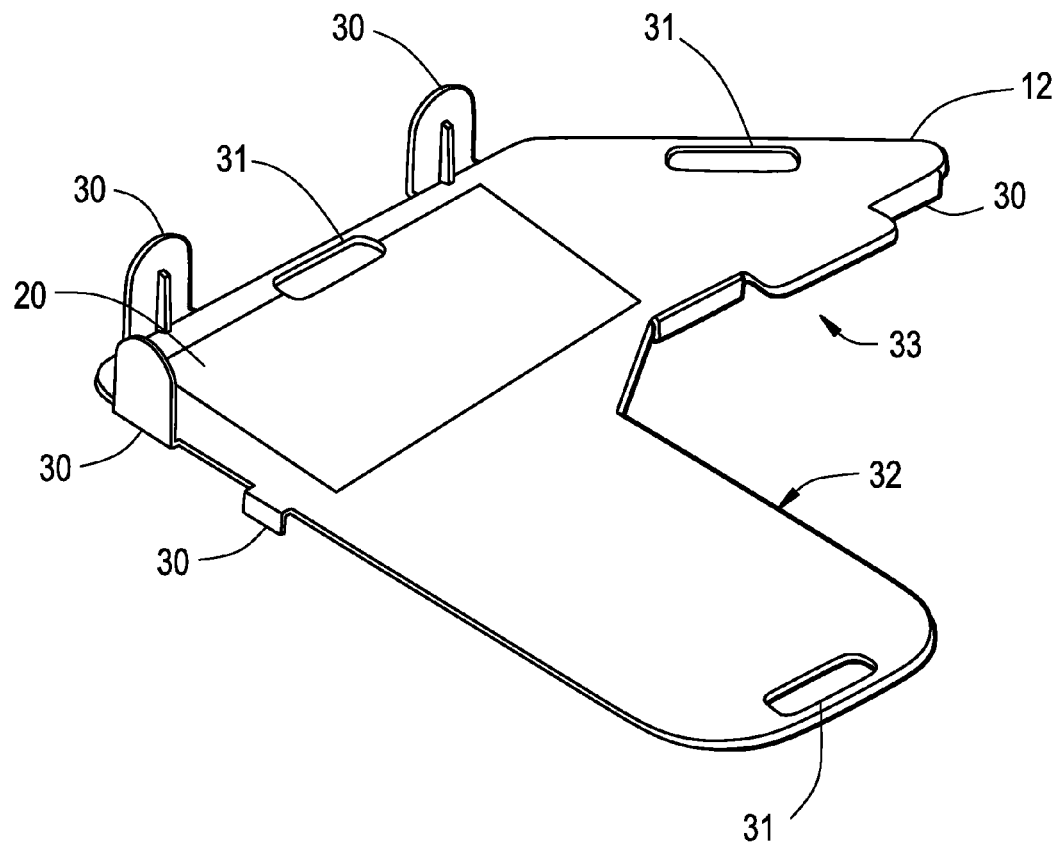
FIGS. 10A, 10B, and 10C are illustrations of arm boards according to a particular embodiment.
Figure 10B:
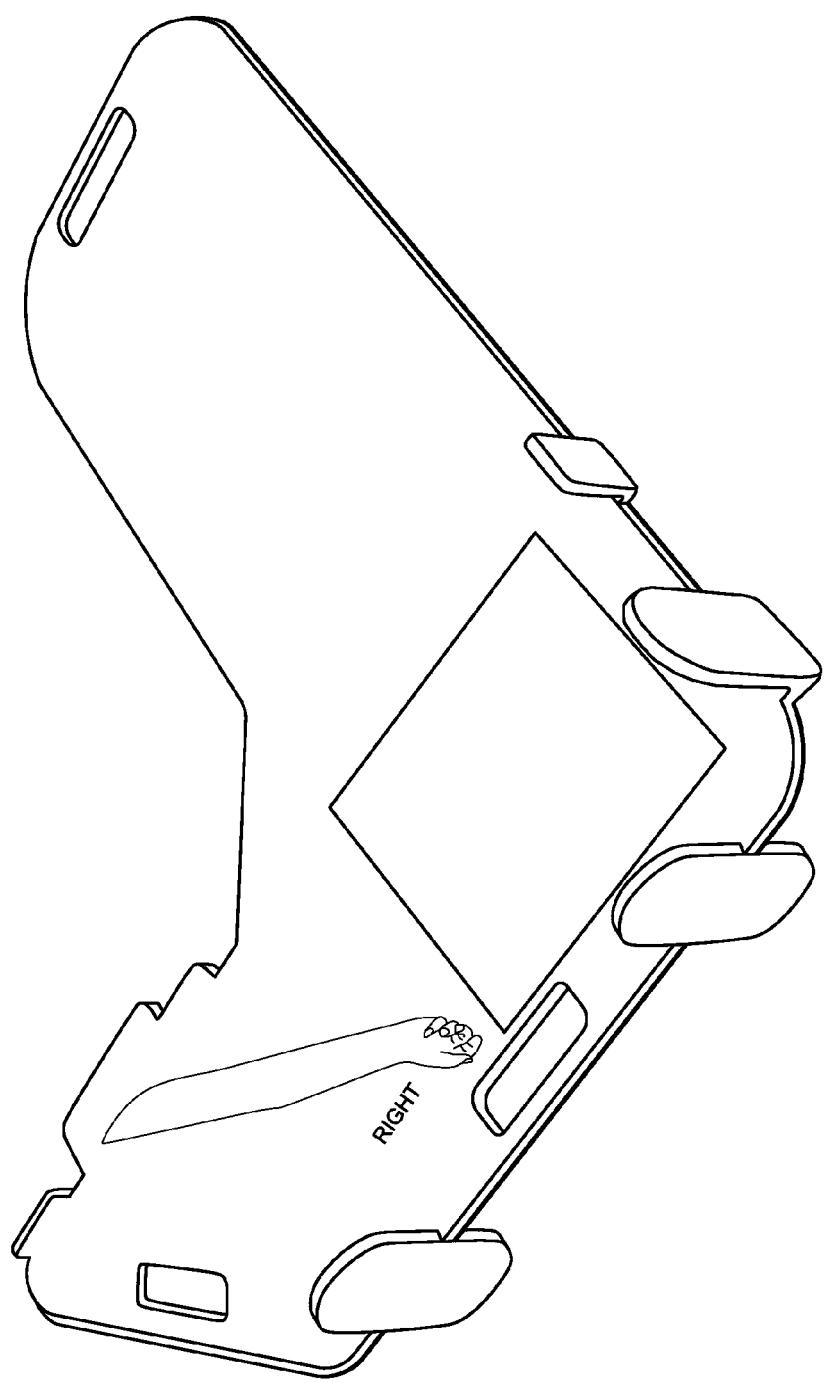
Figure 10C:
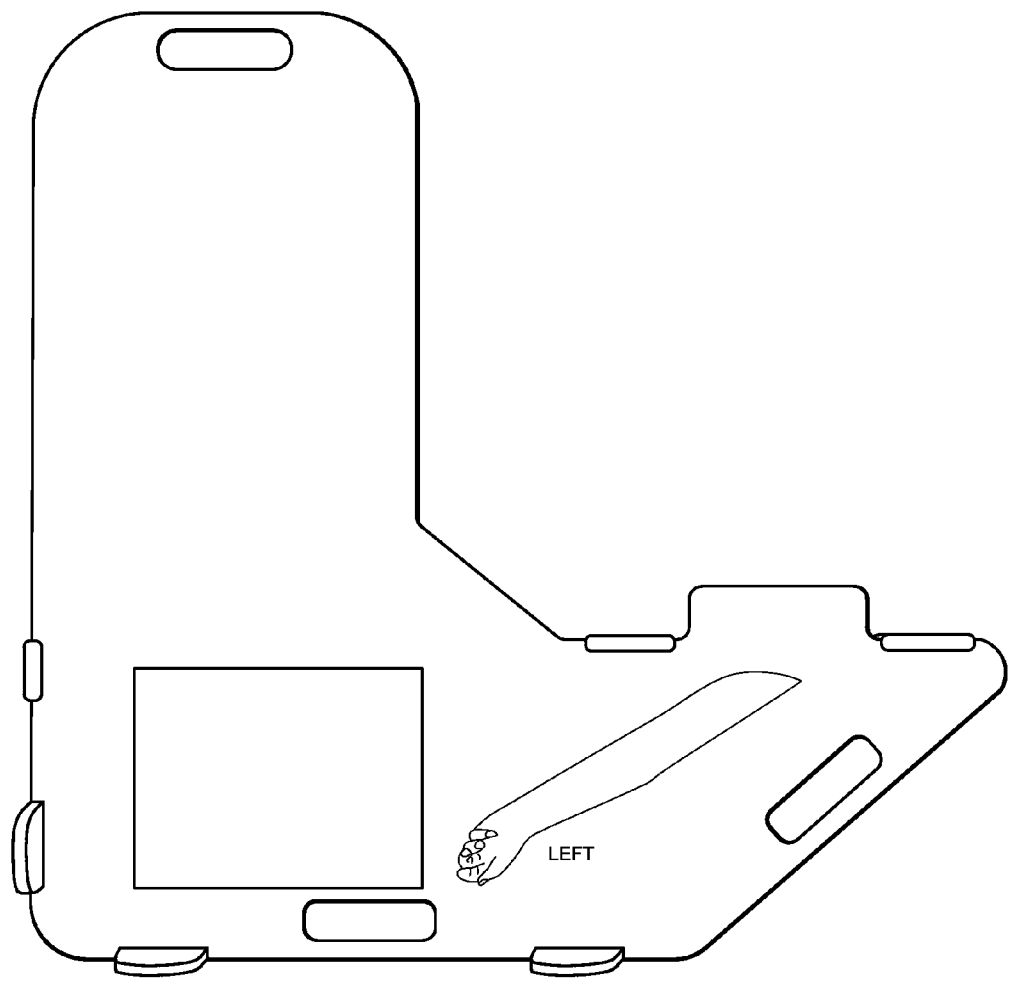

The arm board may further comprise one or more other features to facilitate the use of the arm board for radial cardiac catheterization procedures. For example, in one aspect the arm board 10 comprises a hinge 28 that allows for the rotation of the substantially planar member 12 (FIG. 8). In another aspect the arm board 10 further comprises one or more post members 30 fixed to the member 12 and protruding away from the support surface about an edge of the member (FIG. 9). Such post members 30 may project upward from the arm board to allow for placement of a drape over the patient's arm or may project downward from the arm board to prevent the arm board from encroaching under the patient further than desired (FIG. 10). In still another aspect, the arm board 10 further comprises a means 32 for stabilizing and immobilizing a patient's arm on the support surface (FIG. 9). Such means 32 for stabilizing and immobilizing a patient's arm are well known to those skilled in the art, and often are in the form of flexible straps that can be easily (i.e., hook and loop, etc.) or recesses within which a patient's arm can be immobilized. The arm board 10 still further may comprise a foam or fabric cushion (not illustrated) to both facilitate stabilizing and immobilizing a patient's arm while also facilitating the patient's comfort during the procedure (not shown). In still another aspect, the arm board 10 may further comprise one or more holes 31 to aide in handling the arm board 10 before, during, and after the radial cardiac catheterization procedures (FIG. 10). It also should be appreciated that other elements and features of the arm board can be provided without altering the function and use of the arm board in radial cardiac catheterization procedures.

In one embodiment, the arm board 10 comprises a base member 12 having an L-shape (FIG. 10). The base member 12 may comprise a first portion 32 suitable for sliding under the patient's midsection and a second portion 33 for supporting the patient's arm. In particular embodiments, the first portion 32 of the arm board 10 has a greater width than the second portion 33 of the arm board to assist in the counter-balance of the second portion 33. A radiopaque portion 20 may be disposed within the second portion 33 of the base member 12 in that area which is substantially adjacent to the first portion 32, underneath the area that the patient's hand is placed during catheterization procedures. Not wishing to be bound by any theory, it is believed that this particular configuration is particularly beneficial by reducing the amount of radiation that the patient is exposed to during catheterization procedures. Those skilled in the art will appreciate that imaging equipment automatically increases the dosage of radiation to provide the clearest possible image based on the amount of radiation received from the delivery tube by the image intensifier. Thus, the L-shape embodiment provides an advantage over the C-shape embodiment by reducing the layers of material that the radiation must pass through before penetrating the patient.

Figure 11A:
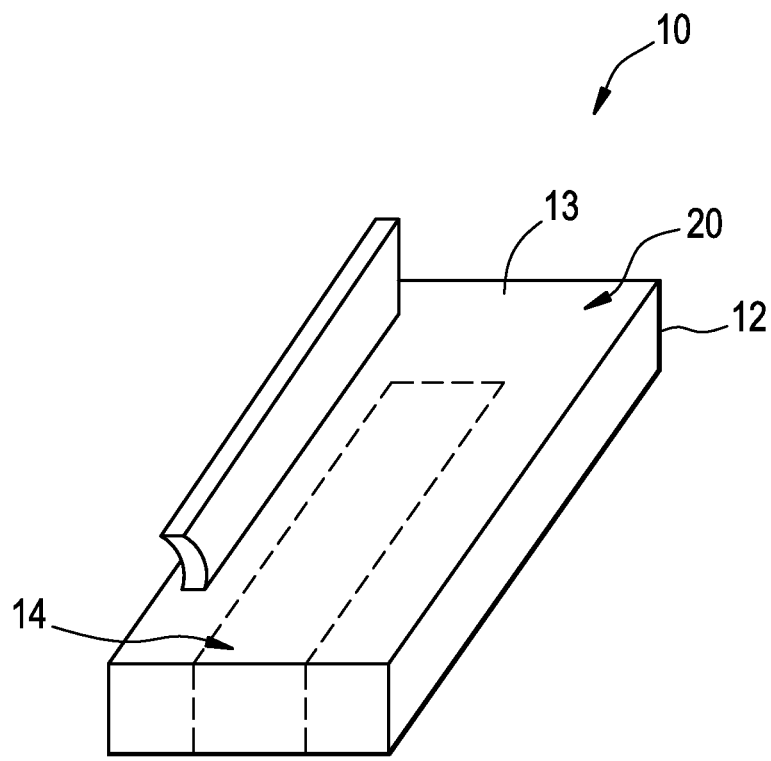
FIG. 11 is a perspective view of an arm board according to a particular embodiment.
Figure 11B:
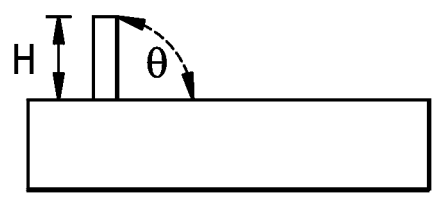

In one aspect, the arm board 10 further comprises at least one shield member 15 affixed to the base member 12 and extending away from the support surface 13 at an angle θ from about 30 and about 90 degrees, at an angle θ from about 60 to about 90 degrees, or at an angle θ of about 90 degrees (FIG. 11). The shield member 15 desirably comprises a radiopaque material, such as the radiation-absorbing materials described above, and is operable to further reduce the doctor's exposure to radiation during a radial cardiac catheterization procedure. For example, in one aspect the shield member may comprise a rigid, thin composite construction comprising a layer of radiopaque material disposed in or around all or a portion of a structural member. The shield member 15 can be any shape that is suitable for reducing a doctor's exposure to radiation during the procedure, provided it does not significantly impair the ability to obtain the necessary medical images during the procedure. For example, the shield member 15 can be rectangular, oblong, or square. Desirably, the shield member 15 has a height (H) from the support surface 13 that is effective for providing protection to the doctor while maintaining a sight-line for safe procedural imaging and patient comfort. For example, in one embodiment the height (H) of the shield member 15 from the support surface 13 is from about 10 cm to about 45 cm, from about 20 cm to about 40 cm, or from about 30 cm to about 40 cm.

Figure 12:
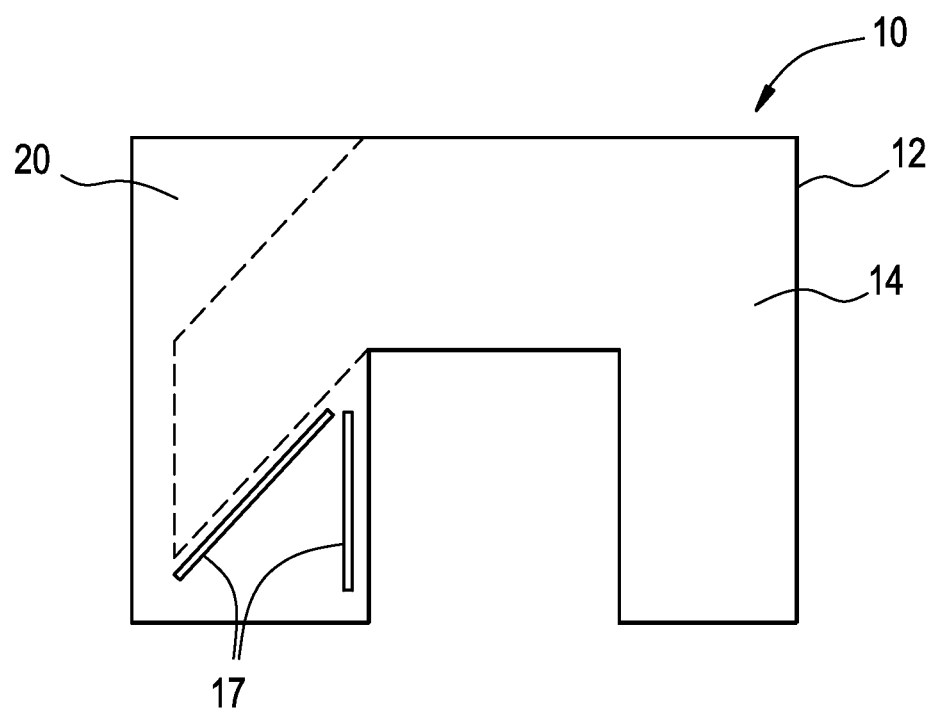
FIG. 12 is an illustration of an arm board according to a particular embodiment.

The shield member 15 may extend from the support surface 13 of the base member 12 at any position suitable for reducing a doctor's exposure to radiation during the procedure, provided that it does not significantly impair the ability to obtain the necessary medical images during the procedure. Accordingly, the shield member 15 desirably is positioned between the doctor and the radiation source. For example, in one aspect the shield member 15 is disposed between the patient's arm and body along a plane that is substantially parallel to the patient's arm or along a plane that is substantially parallel to the patient's body (FIG. 12).

Figure 13A:
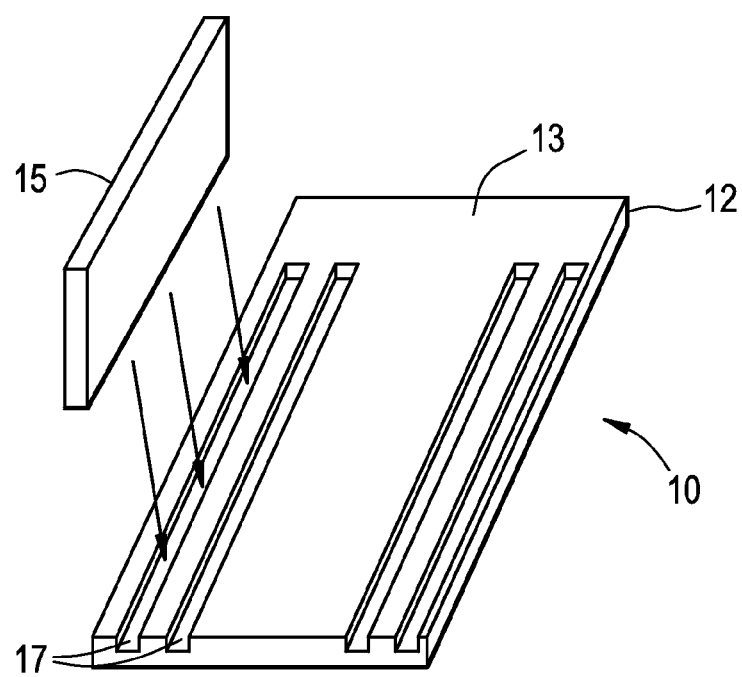
FIGS. 13A and 13B are illustrations of arm boards according to particular embodiments.
Figure 13B:
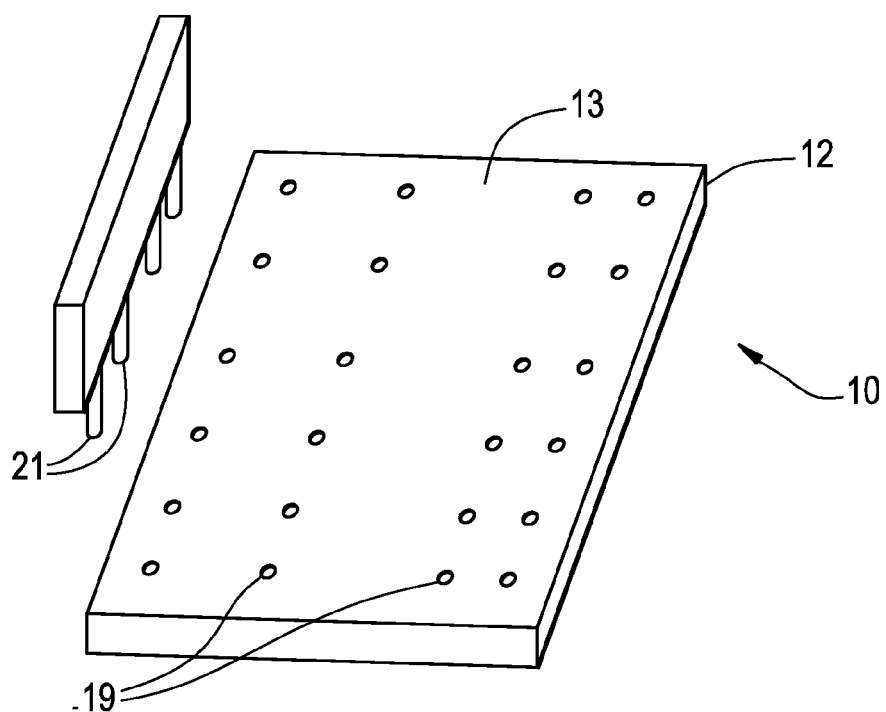

In particular aspects, it is desirable for the shield member 15 to be releasably affixed to the base member 12. The connection between the members can be accomplished by any switchable means known in the art; such as latches, friction fit, snap fit, members, etc. The shield also may be positionally adjustable with respect to the base. For example, it may be continuously adjusted within a range or discretely adjusted. For example, in one aspect the base member 12 may comprise one or more grooves 17 into which at least one mating portion of the shield member 15 can be inserted (FIG. 13A). In another aspect, the base member 12 may comprise a plurality of rows of apertures or slots 19 in which the at least one mating portion 21 (i.e., pins) of the shield member 15 can be inserted (FIG. 13B).

In still another aspect of the present description, the arm board further comprises a sleeve that substantially envelopes the substantially planar support member (not shown). The sleeve can comprise at least one radiolucent portion and at least one radiopaque portion. In one embodiment, the at least one radiopaque portion of the arm board optionally may be disposed in only the sleeve, such that the substantially planar support member of the arm board is comprised of only a substantially radiolucent material. Those skilled in the art should appreciate that such an embodiment could be placed over existing arm boards used in radial cardiac catheterization procedures while still providing many of the same benefits of the present description, including reducing and/or eliminating a doctor's exposure to radiation during radial cardiac catheterization procedures.

B. Medical Apparatus

Figure 14:
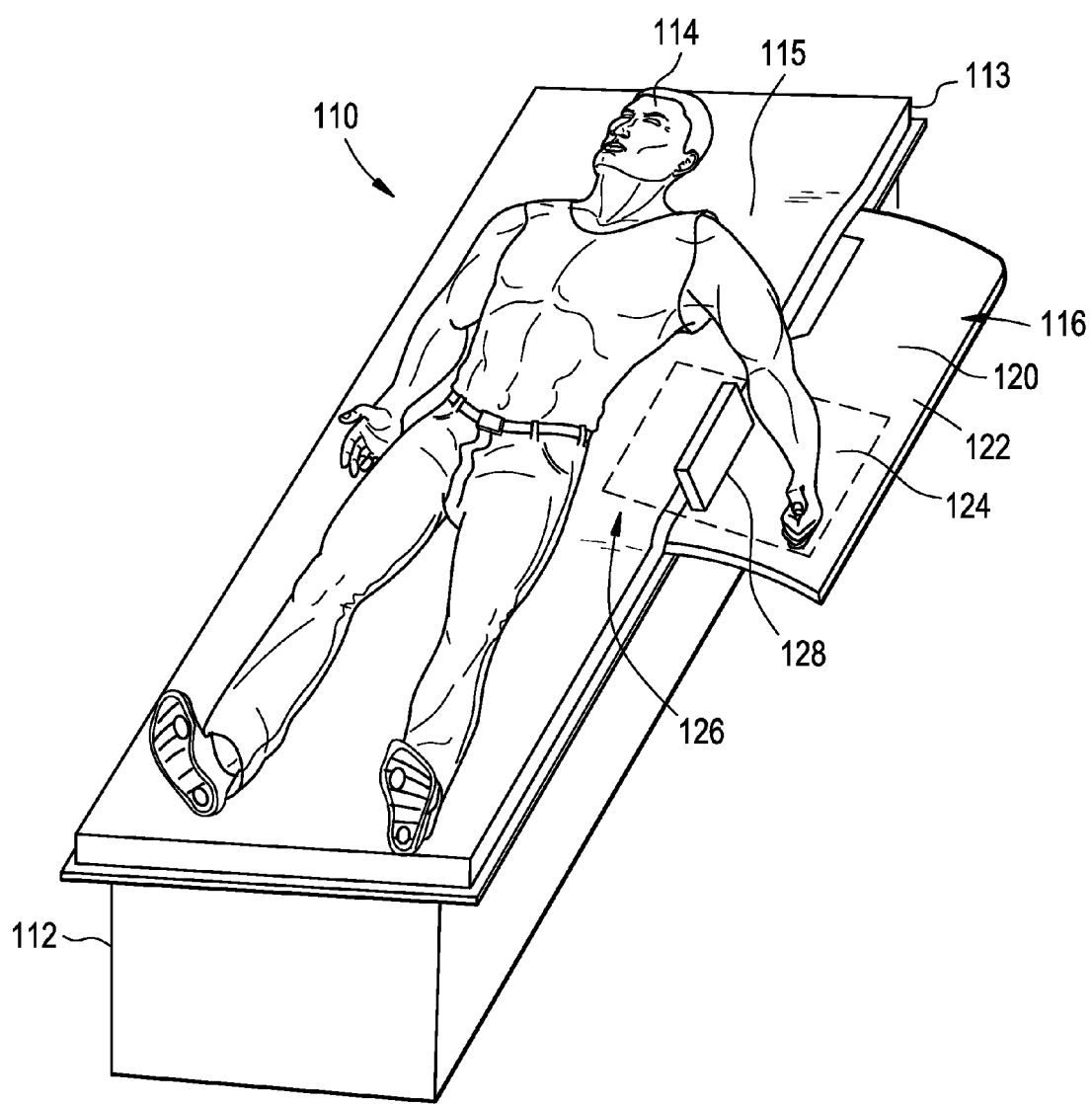
FIG. 14 is an illustration of a medical apparatus for use in supporting a patient lying in a supine position during a radial cardiac catheterization according to a particular embodiment.
Figure 15:
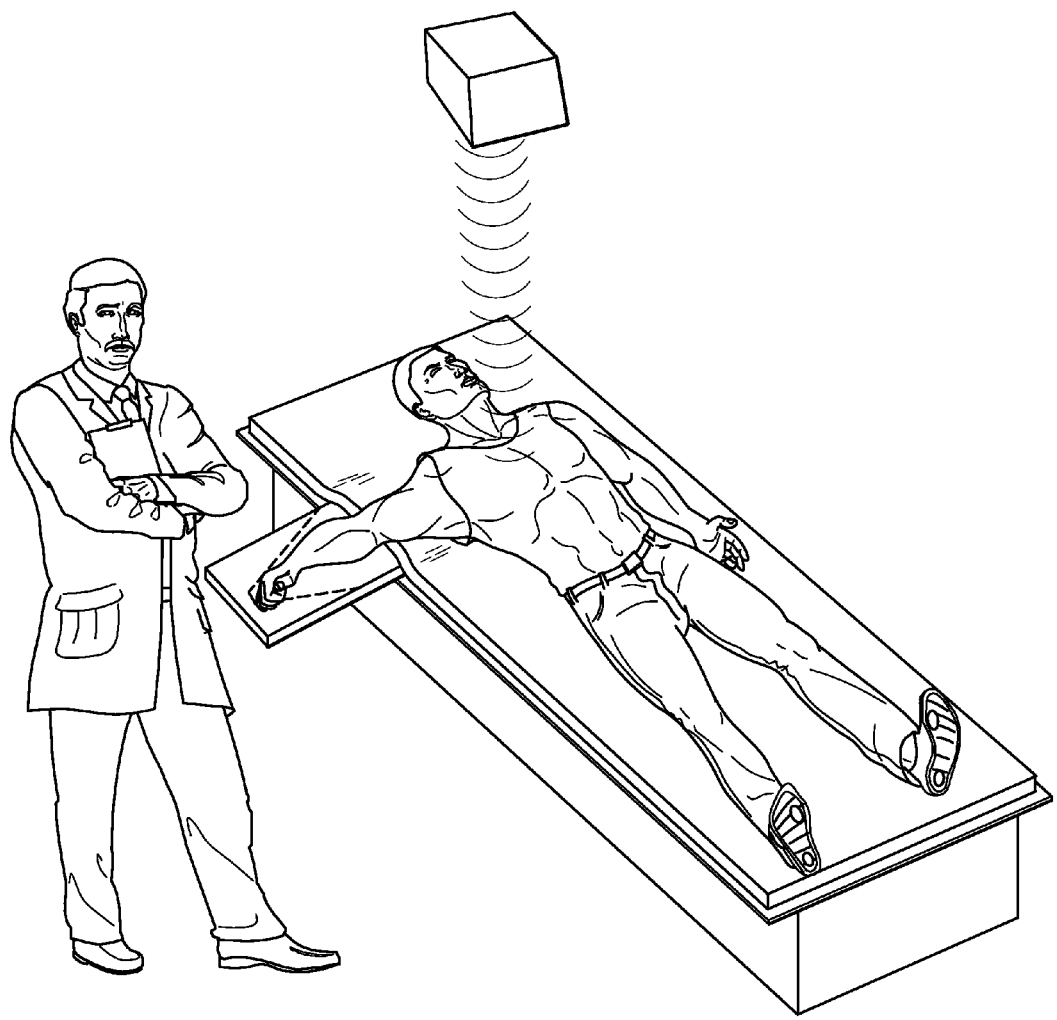
FIG. 15 is an illustration of a method for using the arm board to support a patient's arm during a radial cardiac catheterization according to a particular embodiment.

In another aspect, a medical apparatus is provided for use in supporting a patient lying in a supine position during a radial cardiac catheterization procedure. The medical apparatus 110 (FIG. 14) generally comprises an operating table 112 suitable for supporting a patient 114 lying in the supine position and an arm board 116 secured to the operating table 112. The arm board 116 comprises a substantially planar member 118 having a support surface 120 on which a patient's arm 115 can be stabilized during a catheterization procedure, and comprises a radiopaque portion 122 and a radiolucent portion 124. The arm board 116 further comprises a shield portion 128 extending away from the support surface and disposed between the patient's body and patient's arm 115.

The arm board 116 can be secured to the operating table 112 using any suitable securing means. In one aspect, wherein the operating table 112 comprises a mattress 113, the arm board 116 has a first portion 126 that is reversibly securable between an upper surface of the operating table 112 and the mattress 113. In another aspect, the arm board 116 can be secured to the operating table by means of a hinge or by any other attachment means suitable for reversibly securing the arm board 116 to the operating table 112 (not illustrated).

C. Method

In still another aspect, a method is provided for radial cardiac catheterization of a patient. The method first comprises supporting the arm of a patient lying in a supine position on an operating table by an arm board which extends from the operating table, the arm board having a substantially horizontal and planar support surface on which the arm is stabilized. The method then comprises introducing one or more medical instruments through a catheter in the stabilized arm of the patient and using x-ray imaging (or any other suitable form of medical imaging) to visualize the position of the one or more medical instruments introduced into the patient through the catheter. In one aspect, the arm board comprises a radiolucent portion positioned in the arm board to permit the x-ray imaging (or other forms of medical imaging) and a radiopaque portion surrounding at least part of the radiolucent portion. In another aspect, the arm board comprises an elongated member in which the radiolucent portion of the board extends from a first end of the member along a medial section of the member toward an opposed second end, the first end being proximate the patient's shoulder and the second end being proximate the hand of the catheterized arm of the patient.

Embodiments of the arm board provided herein are operable to reduce and/or eliminate a doctor's exposure to radiation during radial cardiac catheterization procedures when the arm board is used in combination with standard radiation protection (e.g., lead apron and collar, low leaded table-to-floor flaps, mobile leaded glass barriers) as compared to the exposure to use of standard radiation protection without the arm board. For example, in particular embodiments the arm board provided herein reduces the doctor's exposure to radiation by greater than about 25%, by greater than about 35%, or by greater than about 50%.

D. Kits

In still another aspect, kits are provided comprising an arm board for radial cardiac catheterization procedures. The kits may comprise various sizes and shapes of shield members that are designed to mate with given base member. For example, in a particular embodiment the kit may comprise one or more base members of the arm boards and a plurality of sizes and shapes of shield members that may be interchangeably mated with the one or more base members based on the consideration of variables such as the shape and size of the patient, accessibility of the patient's arm during the procedures, and the doctor's personal preferences.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

We claim:

1. An arm board for use in a radial cardiac catheterization procedure comprising:
    a planar base member having a support surface shaped and dimensioned to stabilize a patient's arm in a plane with the body of the patient during a radial catheterization procedure, the planar base member comprising:
        at least one radiolucent portion positioned in the planar base member to permit x-ray imaging of the patient when the planar base member is positioned underneath the patient; and
        at least one radiopaque portion which has an area lateral to at least a portion of an area of the at least one radiolucent portion; and
    at least one shield member affixed to the planar base member and extending away from the support surface, the shield member comprising a radiopaque material,
    wherein the at least one radiopaque portion of the planar base member and the at least one shield member provide radiation attenuation effective to reduce a doctor's exposure to radiation from x-ray imaging when the doctor is performing the radial catheterization procedure on the patient.

2. The arm board of claim 1, wherein the shield member has a height from the support surface from about 10 cm to about 45 cm.

3. The arm board of claim 1, wherein the shield member is releasably affixed to the planar base member.

4. The arm board of claim 1, wherein the planar base member includes a posterior portion for placement under a supine patient during catheterization of the patient's arm secured to the anterior portion of the planar base member.

5. The arm board of claim 1, wherein the planar base member comprises at least one slot or groove into which at least one mating portion of the shield member is inserted.

6. The arm board of claim 1, wherein the shield member extends away from the support surface along a plane parallel to the patient's arm.

7. The arm board of claim 1, wherein shield member extends away from the support surface at an angle from about 30 to about 90 degrees.

8. The arm board of claim 1, wherein the radiopaque material comprises a radiation-absorbing material capable of providing a radiation attenuation equivalence of at least that of a 0.25 mm lead sheet.

9. The arm board of claim 1, wherein the radiopaque material comprises a radiation-absorbing material comprising a metal, metal oxide, metal salt, or alloy comprising a metallic component with an atomic number greater than 45.

10. The arm board of claim 9, wherein the metallic component is selected from the group consisting of antimony, tin, barium, bismuth, cesium, cadmium, indium, rhodium, tungsten, uranium, lead, and combinations thereof.

11. The arm board of claim 1, wherein the radiopaque material comprises a radiation-absorbing material comprising a polymer loaded with a metal selected from the group consisting of antimony, tin, barium, bismuth, cesium, cadmium, indium, rhodium, tungsten, uranium, lead, and combinations thereof.

12. The arm board of claim 1, wherein the arm board is effective to reduce a physician's exposure to radiation during the radial cardiac catheterization by more than 25%.

13. The arm board of claim 1, wherein the arm board is effective to reduce a physician's exposure to radiation during the radial cardiac catheterization by more than 50%.

14. A method for radial cardiac catheterization of a patient by a physician, comprising:
   supporting the arm of a patient lying in a supine position on an operating table, wherein the arm is supported by an arm board which extends from the operating table, the arm board comprising a base member having a horizontal and planar support surface on which the arm is stabilized in a plane with the body of the patient and at least one shield member affixed to the base member and extending away from the support surface;
   introducing one or more medical instruments through a catheter in the stabilized arm of the patient; and
   using x-ray imaging to visualize the position of the one or more medical instruments introduced into the patient through the catheter,
   wherein the base member of the arm board comprises a radiolucent portion positioned in the arm board to permit said x-ray imaging and a radiopaque portion surrounding at least part of the radiolucent portion,
   wherein the shield member of the arm board comprises a radiopaque material, and
   wherein the radiopaque portion of the base member and the at least one shield member provide radiation attenuation effective to reduce the physician's exposure to radiation from said x-ray imaging.

15. The method of claim 14, wherein the shield member is disposed between the arm and torso of the patient.

16. The method of claim 14, wherein the arm board operates to reduce the physician's exposure to radiation during the radial cardiac catheterization by more than 25%.

17. The method of claim 14, wherein the arm board operates to reduce the physician's exposure to radiation during the radial cardiac catheterization by more than 50%.

* * * * *